(12) United States Patent
Ostermeier et al.

(10) Patent No.: US 11,510,812 B2
(45) Date of Patent: Nov. 29, 2022

(54) INJECTOR FOR OCULAR IMPLANT

(71) Applicant: Implandata Ophthalmic Products GmbH, Hannover (DE)

(72) Inventors: Max Ostermeier, Seevetal (DE); Stefan Meyer, Hannover (DE)

(73) Assignee: Implandata Ophthalmic Products GmbH, Hannover (DE)

( * ) Notice: Subject to any disclaimer, the term of this patent is extended or adjusted under 35 U.S.C. 154(b) by 943 days.

(21) Appl. No.: 16/330,045

(22) PCT Filed: Sep. 4, 2017

(86) PCT No.: PCT/US2017/072094
§ 371 (c)(1),
(2) Date: Mar. 1, 2019

(87) PCT Pub. No.: WO2018/042033
PCT Pub. Date: Mar. 8, 2018

(65) Prior Publication Data
US 2021/0275355 A1 Sep. 9, 2021

(30) Foreign Application Priority Data
Sep. 2, 2016 (DE) .......................... 102016116507.7

(51) Int. Cl.
*A61F 9/007* (2006.01)
*A61B 5/00* (2006.01)
(Continued)

(52) U.S. Cl.
CPC ............ *A61F 9/00781* (2013.01); *A61B 3/16* (2013.01); *A61B 5/6847* (2013.01);
(Continued)

(58) Field of Classification Search
CPC ................ A61B 2560/063; A61B 3/16; A61B 2562/0247; A61B 17/3468; A61F 2/1675;
(Continued)

(56) References Cited

U.S. PATENT DOCUMENTS 6,156,042 A * 12/2000 Aramant ............. A61F 9/00727
623/4.1
2001/0020171 A1 * 9/2001 Heyman ............... A61F 2/1678
606/107

(Continued)

OTHER PUBLICATIONS

International Search Report dated Nov. 7, 2017, in International Patent Application No. PCT/EP2017/072094 (2pgs).

*Primary Examiner* — Javier G Blanco
(74) *Attorney, Agent, or Firm* — North Weber & Baugh LLP; Michael North

(57) ABSTRACT

An injector (1) for implanting a sensor implant (2) in the human or animal eye, in particular for the suprachoroidal implantation of a pressure sensor for the wireless measurement of the intraocular pressure, is improved in terms of rapid, complication-free, low-trauma and low-wear suprachoroidal implantation in that, to accommodate the sensor implant, the injector (1) has a substantially tubular injection chamber (8), the inner wall surfaces (9, 10) of which have a non-rotationally symmetrical cross section, preferably an oval or rectangular cross section, in that, at a free end, the injection chamber (8) is provided with an injection opening (13), through which, during implantation, the sensor implant (2) can slide out and slide into a sclera incision in the eye, wherein the inner wall surfaces (9, 10) of the injection chamber (8) enclose the likewise non-rotationally symmetrical cross section of the sensor implant (8) and prevent a rotation of the sensor implant (2) about an axis of rotation extending in the direction of the injection (11).

7 Claims, 6 Drawing Sheets

(51) Int. Cl.
*A61B 3/16* (2006.01)
*A61F 9/00* (2006.01)

(52) U.S. Cl.
CPC ...... *A61F 9/0017* (2013.01); *A61B 2560/063* (2013.01); *A61B 2562/0247* (2013.01)

(58) Field of Classification Search
CPC ...... A61F 2/167; A61F 9/0008; A61F 9/0017; A61F 9/00781
See application file for complete search history.

(56) References Cited

U.S. PATENT DOCUMENTS

| | | | |
|---|---|---|---|
| 2008/0119865 A1 | 5/2008 | Meunier et al. | |
| 2010/0331868 A1* | 12/2010 | Bardy | A61M 37/0069 606/167 |

* cited by examiner

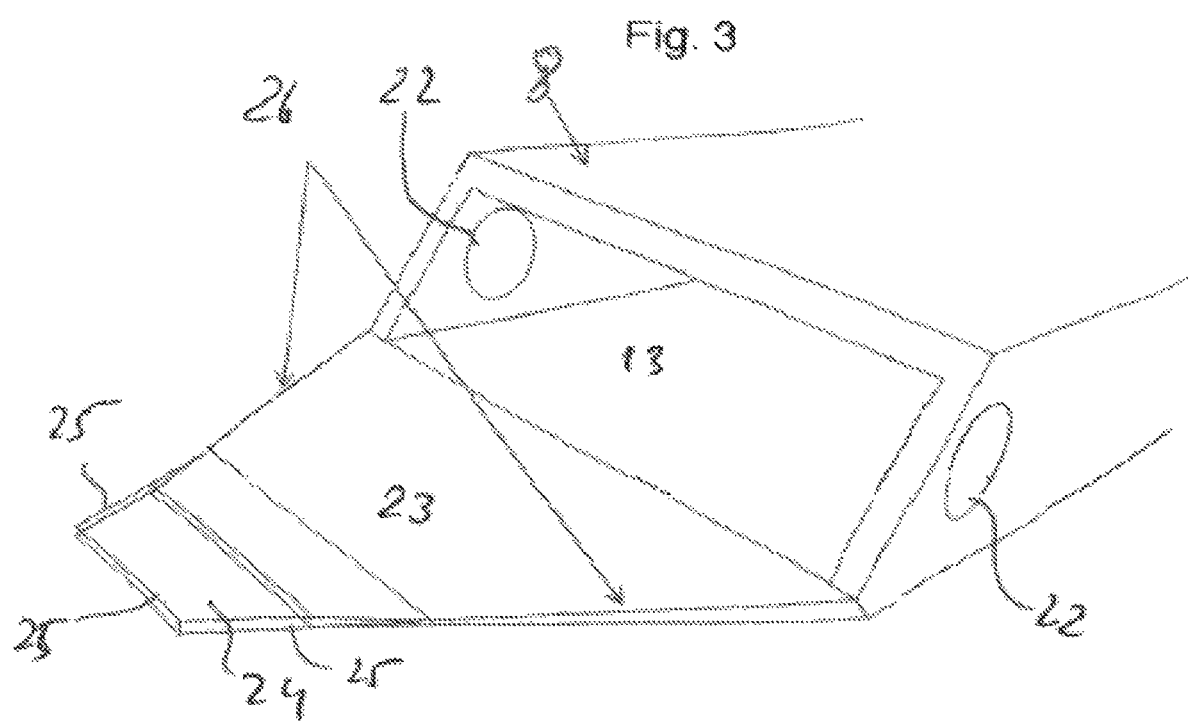

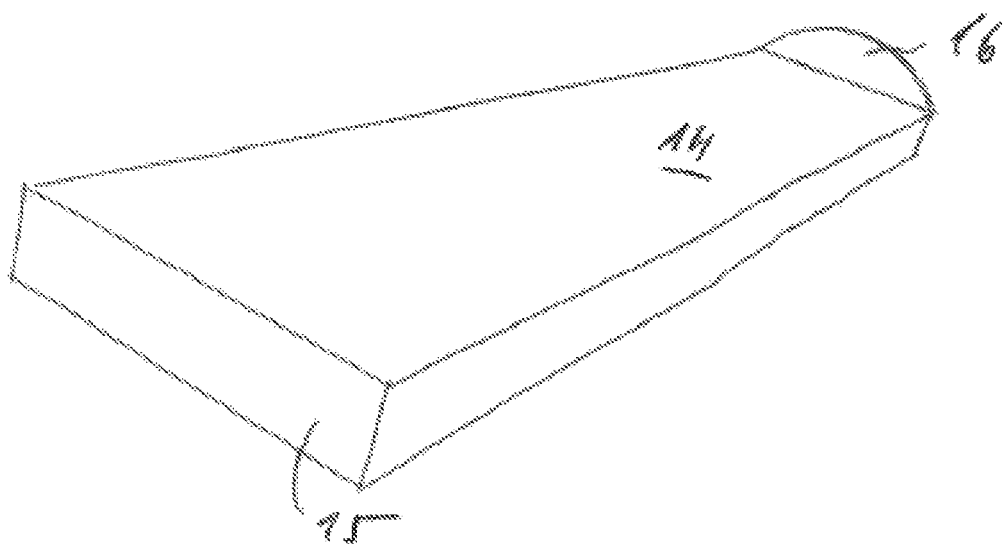

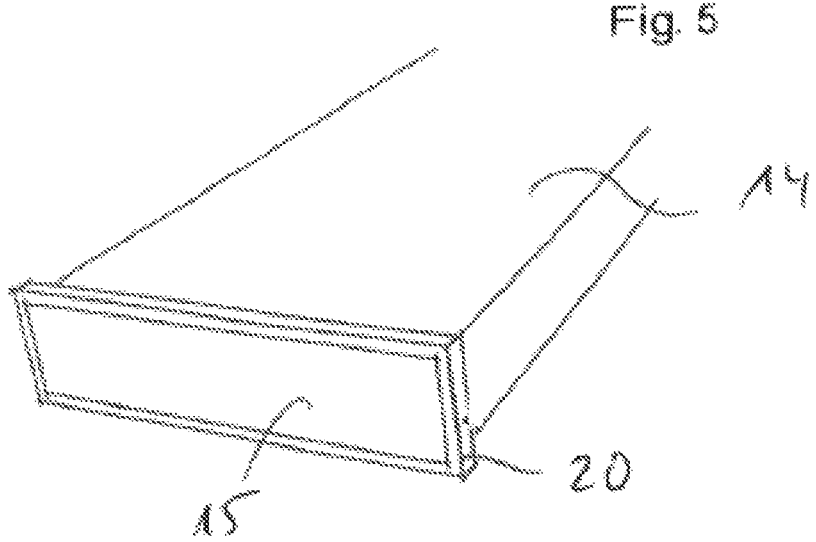

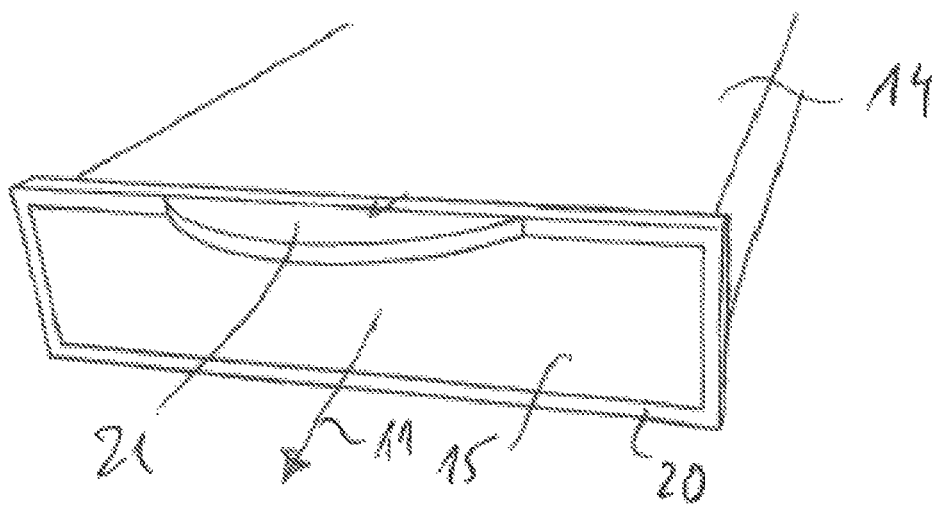

INJECTOR FOR OCULAR IMPLANT

CROSS-REFERENCE TO RELATED APPLICATIONS

This application is a US National Stage Entry Under 35 USC § 371 of International Patent Application No. PCT/EP2017/072094, entitled "INJECTOR FOR OCULAR IMPLANT," naming as inventors Max Ostermeier and Stefan Meyer, and filed Sep. 4, 2017, which claims priority to German Patent Application No. 102016116507.7, filed Sep. 2, 2016, which applications are hereby incorporated herein by reference in their entireties.

The invention relates to an injector for the implantation of a sensor implant into the human or animal eye, in particular for the suprachoroidal implantation of a pressure sensor for the wireless measurement of the intraocular pressure.

Injectors for lens implants are known in conjunction with cataract operations, in which the artificial lens to be implanted is folded and introduced through a narrow channel into an incision in the eye. However, these known injectors are not suitable for the suprachoroidal implantation of sensor implants. Such sensor implants are typically inserted by means of tweezers into an incision previously introduced into the eyeball, which is linked to risks for the patient, because the hazard of damage to the choroid with uncontrollable bleeding exists in this case.

Furthermore, the sensor implant has to be introduced in a specific orientation into an artificially provided pocket between the sclera and the choroid, so that the pressure sensor attached on one side of the sensor implant can measure the correct intraocular pressure.

The object of the invention is therefore to specify an injector for the implementation of a sensor implant into the human or animal eye, using which a typical sensor implant is implantable rapidly, with little trauma, and in a manner gentle to the material into a suprachoroidal pocket of the eye.

The solution according to the invention is that the injector has a substantially tubular injection chamber for receiving the sensor implant, the inner wall surfaces of which have a non-rotationally symmetrical cross section, preferably an oval or rectangular cross section, the injection chamber is provided at a free end with an injection opening, through which the sensor implant can slide out during the implantation and can slide into an incision in the eye, wherein the inner wall surfaces of the injection chamber enclose the cross section of the sensor implant, which is likewise non-rotationally symmetrical, and prevent a rotation of the sensor implant about an axis of rotation lying in the injection direction.

Typical housings of such sensor implants have a flat oblong shape, for example, an ellipsoid or a cuboid having rounded corners and edges. If such a sensor implant is located in the tubular injection chamber, its longitudinal axis is thus aligned substantially parallel to the longitudinal axis of the injection chamber and thus to the injection direction. The sensor implant therefore cannot rotate in the injection chamber about an arbitrary axis which is perpendicular to the injection direction. Because of its non-rotationally symmetrical cross section and the likewise non-rotationally symmetrical cross section of the inner wall surfaces of the injection chamber, the sensor implant also cannot rotate about an axis lying in the injection direction, because it is "flat" in cross section, i.e., its width is greater than its thickness.

A suprachoroidal implantation only becomes possible due to this flat shape, because a pocket to be formed between the sclera and the choroid can only have a limited width, because otherwise discomfort would be experienced by the patient. A typical thickness of the sensor implant is 2 mm or less. Its width is preferably less than 3.5 mm and the length is typically 7 mm or less. The pressure sensor is typically housed in one of the two large surfaces of the sensor implant. The surface provided with the pressure sensor has to face toward the center of the eye and thus the choroid when the sensor implant is implanted, so that the pressure sensor can correctly measure the intraocular pressure. If the side of the sensor implant provided with the pressure sensor faced toward the outer side of the eye and thus the sclera, the obtained measured values thus would not be correlated with the intraocular pressure. The correct attitude of the sensor implant in the subchoroidal pocket of the eye is thus decisive for correct measured values.

The injector according to the invention has the advantage that the sensor implant is always implanted in the correct attitude, and the implantation is performed rapidly and with little trauma in comparison to the use of tweezers.

In one preferred embodiment of the invention, the injector has a slide, using which the sensor implant can be pressed out of the injection chamber through the injection opening. Due to the connection of the injector and the slide, it is always available in the correct position.

In an advantageous embodiment of the invention, the cavities between the inner wall surfaces of the injection chamber and the sensor implant are filled with a viscoelastic material, preferably with hyaluronic acid. The viscoelastic material is used in this case as a lubricant to reduce the friction between the inner wall surfaces of the injection chamber and the sensor implant. Moreover, parts of the viscoelastic material remain adhering to the sensor implant when it leaves the injection opening and slides into the incision in the eye, wherein the friction is also reduced and the sliding is facilitated in the eye.

In an alternative embodiment, a first chamber portion of the injection chamber located between the injection opening and the sensor implant is filled with the viscoelastic material, preferably with hyaluronic acid, and the sensor implant, which is initially placed into a second chamber portion of the injection chamber more remote from the injection opening, can be pressed through the filled first chamber portion out of the injection chamber. At the same time, the sensor implant is immersed in the viscoelastic material and is completely wetted thereby before it leaves the injection opening.

In an advantageous refinement of the invention, it is provided that the second chamber portion is designed as a loading chamber having a lateral loading opening for inserting the sensor implant. The "dry" loading chamber can be opened by means of the loading opening without the risk of escape of viscoelastic material existing. After the insertion of the sensor implant into the loading chamber and the closing of the loading opening, the sensor implant is then pushed by means of the slide into the second chamber portion filled with viscoelastic material and wetted by the viscoelastic material at the same time, before it is pressed out through the injection opening.

The invention can also be improved by the measure that the slide is provided with a peripheral sealing lip in order to press the sensor implant hydraulically out of the injection chamber with the aid of the viscoelastic material. In the ideal case, the slide therefore does not even have to touch the sensor implant, because it presses the viscoelastic material, which is used here as a hydraulic fluid, in the direction of the injection opening and out of this opening, wherein the viscoelastic material carries along the sensor implant. In this embodiment, it is also possible to firstly press a certain volume of the viscoelastic material into the sclera incision in the eye, in order to first provide a subchoroidal pocket between the sclera and the choroid in this manner, in which the sensor implant is then received.

In order to avoid rising or slipping of the implant inserted in the loading chamber during actuation of the slide, it is recommended that the slide be provided with a stopper protruding in the injection direction in the region of the sealing lip.

To avoid the occurrence of an excessively strong overpressure in the suprachoroidal cavity during the implantation, an embodiment of the invention is recommended in which the injection chamber is provided with lateral outflow openings for the viscoelastic material. At a given advance speed of the slide, the maximum generated pressure in the suprachoroidal cavity is substantially dependent on the cross section and the number of the outflow openings and can thus be limited in the upper direction by selection of the parameters.

A further preferred design feature of the invention is that a trocar protruding in the injection direction having trocar edges tapering obliquely toward one another toward its free end is arranged in the region of the injection opening. During the implantation, the trocar is inserted as a guide tip into the prepared sclera incision. The injection opening of the injector is thus correctly positioned in relation to the sclera incision.

The trocar can be embodied as atraumatic having rounded trocar edges. In this case, the sclera has to be opened to the required width before the implantation.

However, the trocar can also be provided with sharp trocar edges, by means of which an initially small sclera incision can be widened to the required width. In this case, however, the trocar tip would be embodied as rounded to avoid undesired injuries to the eye.

The trocar tip could also be embodied as bent toward the sclera inner surface in order to avoid unintentional puncture of the choroid.

All mentioned embodiments of the trocar are associated with the present invention.

An embodiment of the invention is also advantageous in which the injector is designed as a sterile disposable device having a preloaded sensor implant. In this embodiment, there can be no error with respect to the attitude of the sensor implant during the insertion into the injector. Furthermore, this embodiment has the advantage that the unintentional introduction of bacteria into the injector is precluded.

BRIEF DESCRIPTION OF THE DRAWINGS

Embodiments of the invention will be explained in greater detail hereafter on the basis of the drawings. In the specific drawings:

FIG. 3 shows an enlarged detail of the injector from FIG. 1;

FIG. 4 shows a slide of the injector from FIG. 1 without a sealing lip;

FIG. 5 shows an enlarged detail of a slide having a sealing lip;

FIG. 6 shows an enlarged detail of a slide having a sealing lip and a stopper.

DETAILED DESCRIPTION

Figure 1:
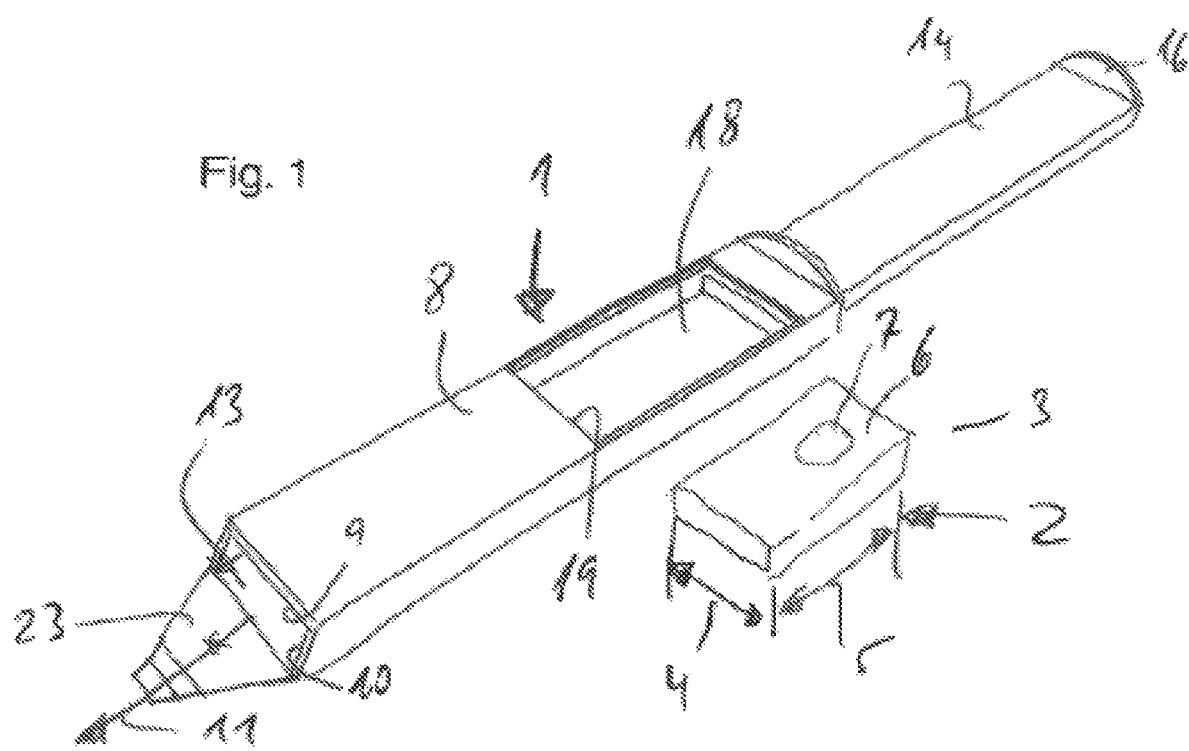
FIG. 1 is a perspective view of an injector according to the invention having a sensor implant before the insertion into the injector.

An injector 1 for the implantation of a sensor implant 2 into a suprachoroidal pocket of the eye can be seen in FIG. 1. The sensor implant 2 is used for measuring the intraocular pressure. It has the form of a cuboid having a relatively low thickness 3, which is preferably less than 2 mm, and a width 4 which is approximately 3.5 mm or less, and a length 5 which is to be less than 7 mm. On one of its large lateral surfaces 6, the sensor implant 2 has a pressure sensor 7, which has to bear on the choroid after the implantation into a suprachoroidal pocket of the eye, in order to measure the intraocular pressure correctly.

The injector 1 has a tubular injection chamber 8, the inner wall surfaces 9, 10 of which have a non-rotationally symmetrical cross section, namely a rectangular cross section having two opposing wide wall surfaces 9 and two opposing narrow wall surfaces 10. The injection chamber 8 is used to receive the sensor implant 2, which also has a rectangular cross section having a greater width 4 and a lesser thickness 3. The width 4 of the sensor implant is somewhat less than the dimension of the wide wall surface 9 and the thickness 3 of the sensor implant is somewhat less than the dimension of the narrow wall surface 10, so that the inner wall surfaces 9, 10 of the injection chamber 8 enclose the sensor implant 2 with play. The sensor implant 2 is thus slightly displaceable inside the tubular injection chamber 8 in the injection direction 11. On the other hand, the non-rotationally symmetrical cross sections of the injection chamber 8, on the one hand, and of the sensor implant 2, on the other hand, prevent a rotation of the sensor implant 2 about an axis lying in the injection direction 11. Since the sensor implant 2 has a length 5 which is greater than the wide wall surfaces 9 of the injection chamber 8, the sensor implant inside the injection chamber 8 also cannot rotate about an axis of rotation 12 pointing perpendicularly to the injection direction 11 or about any arbitrary other axis of rotation.

The injection chamber 8 has an injection opening 13 at its free end, through which the sensor implant 2 passes in the injection direction 11 during the implantation and can be pressed out of the injection chamber 8 into the sclera incision (not shown) in the eye. A slide 14, which is mounted in a sliding manner on the injector 1 like an injection syringe, is used for pressing the sensor implant 2 out of the injection chamber 8. During the implantation, the slide 14 is pressed into the injection chamber 8, wherein it pushes the sensor implant 2 out of the injection opening 3. The slide 14 can be actuated manually, by a suitable mechanism, or by a motor.

In the enlarged view in FIG. 4, the cuboid formation of the slide can be seen having a narrow end face 15, the rectangular cross section of which is adapted to the dimensions of the inner wall surfaces 9, 10 of the injection chamber 8. In a first embodiment, the narrow end face 15 is also used as the contact surface in relation to the sensor implant 2, in order to press it through the injection chamber 8 out of the injection opening 13. The other end of the cuboid slide 14 is provided with a widening 16, which facilitates the manual actuation of the slide 14.

To reduce the friction between the inner wall surfaces 9, 10 of the injector, on the one hand, and the outer surfaces of the sensor implant 2, on the other hand, the injection chamber 8 is provided with a viscoelastic material, in the present case with hyaluronic acid, which fills up the cavities between the inner wall surfaces 9, 10 and the outer surfaces of the sensor implant 2 and is used as a lubricant.

Figure 2:
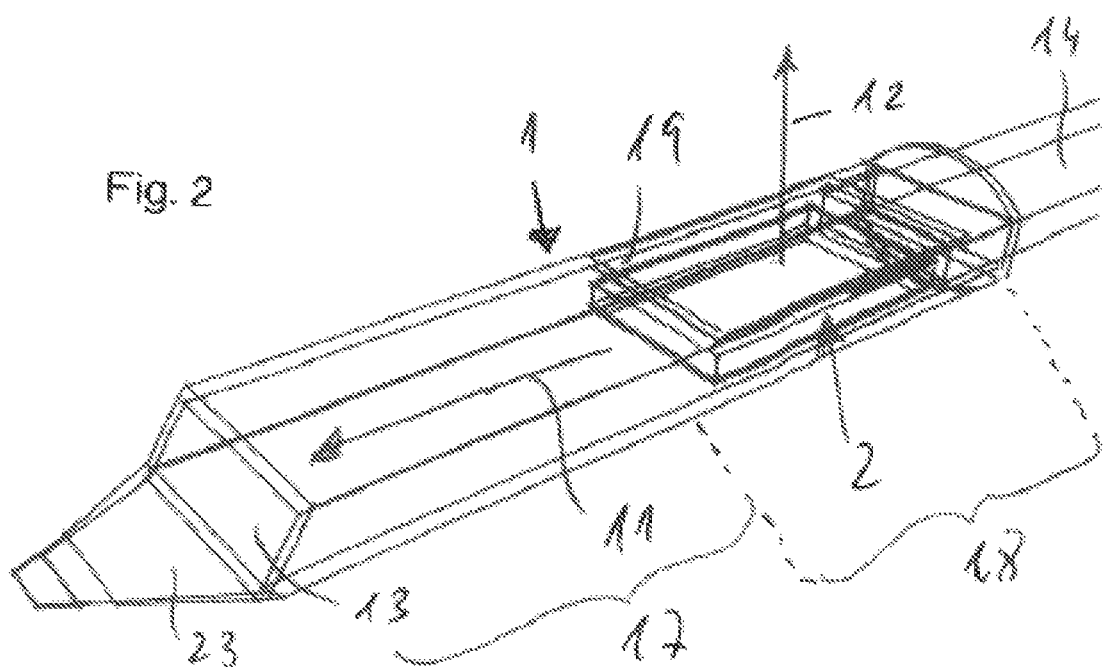
FIG. 2 is as in FIG. 1, but with the sensor implant inserted into the injector.

In a second embodiment of the invention, a first chamber portion 17 of the injection chamber 8 located between the injection opening 13 and the sensor implant 2 is filled with hyaluronic acid. An adjacent second chamber portion is designed as a loading chamber 18. See FIG. 2 in particular in this regard. The loading chamber 18 has a loading opening 19, through which the sensor implant 2 can be inserted into the loading chamber 18. The sensor implant 2 can then be pushed by the slide 14 out of the loading chamber 18 into the first chamber portion 17, where it is immersed in the hyaluronic acid and is wetted thereby, before it exits through the injection opening 13.

In a second embodiment shown in FIG. 5, the slide 14 is provided with a peripheral sealing lip 20, which seals the slide 14 in relation to the inner wall surfaces 9, 10 of the injection chamber 8 upon entry of the sealing lip 20 into the first chamber portion 17, so that the sensor implant 2 can be hydraulically pressed out of the injection chamber 8 with the aid of the hyaluronic acid.

In a further embodiment shown in FIG. 6, the slide 14 is additionally provided in the region of the sealing lip 20 with a stopper 21 protruding in the injection direction 11, which stopper prevents rising or slipping of the sensor implant inserted into the loading chamber 18 during actuation of the slide 14.

As can be seen in FIG. 3, the injection chamber 8 is provided with two lateral outflow openings 22, from which excess hyaluronic acid can escape during the actuation of the slide 14 in the course of the implantation, so that the pressure of the hyaluronic acid in the suprachoroidal pocket of the eye does not become excessively large.

The injector 1 is provided with a trocar 23 in the region of the injection chamber 13. As can be seen best in FIG. 3, the trocar 23 has a trocar tip 24, the lateral edges 25 of which are formed rounded, to avoid undesired injuries to the eye during the implantation. The trocar tip 24 can also be bent upward, i.e., toward the sclera inner surface, to avoid unintentional puncture of the choroid. Furthermore, the trocar 23 has trocar edges 26 tapering toward one another obliquely, which can be formed rounded in an atraumatic manner to avoid undesired cuts during the implantation. In a modified embodiment, the trocar edges 26 can also be embodied as sharp-edged, however, to optionally widen a relatively small sclera incision during the implantation so that the sensor implant 2 passes through it.

LIST OF REFERENCE NUMERALS 1 injector
2 sensor implant
3 thickness
4 width
5 length
6 lateral surface
7 pressure sensor
8 injection chamber
9 wide wall surface
10 narrow wall surface
11 injection direction
12 axis of rotation
13 injection opening
14 slide
15 narrow end face
16 widening
17 first chamber portion
18 second chamber portion/loading chamber
19 loading opening
20 sealing lip
21 stopper
22 outlet openings
23 trocar
24 trocar tip
25 edges
26 trocar edges

The invention claimed is:

1. An intraocular pressure sensor injector for implanting an intraocular pressure sensor into a suprachoroidal space of an eye, the injector comprising:
    a substantially tubular injection chamber for receiving the sensor, the chamber comprising inner wall surfaces having a non-rotationally symmetrical cross section;
    an injection opening positioned at a first end of the injector, the injector opening allowing the sensor to slide from the chamber into a sclera incision in the eye; and
    a slide within the injector that allows the sensor to be pressed out of the injection chamber through the injection opening;
    wherein the inner wall surfaces of the injection chamber enclose non-rotationally symmetrical cross section of the sensor and prevent a rotation of the sensor about an axis of rotation relative to a direction of the injection of the sensor,
    wherein the injector further comprises:
        a first chamber portion within the injection chamber positioned between the injection opening and the sensor, the first chamber being filled with a viscoelastic material;
        a second chamber portion within the injection chamber, the second chamber portion having a loading opening for initially receiving the sensor, the second chamber portion sized and configured to facilitate the sensor being pushed through the first chamber portion; and
        a trocar arranged in the region of the injection opening and protruding in the direction of injection direction, the trocar having edges tapering obliquely toward one another and toward a trocar tip having rounded edges,
    wherein the non-rotationally symmetrical cross section of the injection chamber is a rectangular cross section, and wherein the non-rotationally symmetrical cross section of the sensor is a rectangular cross section.

2. The injector of claim 1 wherein the viscoelastic material comprises hyaluronic acid.

3. The injector of claim 1 wherein the slide comprises a peripheral sealing lip to press the sensor hydraulically out of the injection chamber with the aid of the viscoelastic material.

4. The injector of claim 3 wherein the slide is positioned relative to the sealing lip with a stopper protruding in the direction of injection.

5. The injector of claim 1 wherein the second chamber portion is designed as a loading chamber having a lateral loading opening for inserting the sensor.

6. The injector of claim 1 wherein the injection chamber is provided with lateral outflow openings for the viscoelastic material.

7. The injector of claim 1 wherein the injector is designed as a sterile disposable device having a preloaded sensor implant.

* * * * *